United States Patent [19]

Klemm et al.

[11] 4,322,439

[45] Mar. 30, 1982

[54] ω-[2-(N-LOWER ALKYL-BENZAMIDO)-PHENYL]-ALKANOIC ACIDS, THEIR USE, AND MEDICAMENTS CONTAINING THEM

[75] Inventors: Kurt Klemm, Allensbach; Uwe Krüger, Constance; Erich Rapp, Radolfzell; Horst Wolf, Constance; Ekkehard Kraas, Allensbach, all of Fed. Rep. of Germany

[73] Assignee: BYK Gulden Lomberg Chemische Fabrik GmbH, Constance, Fed. Rep. of Germany

[21] Appl. No.: 170,666

[22] PCT Filed: Feb. 2, 1979

[86] PCT No.: PCT/EP79/00006
§ 371 Date: Sep. 21, 1979
§ 102(e) Date: Sep. 21, 1979

[87] PCT Pub. No.: WO79/00586
PCT Pub. Date: Aug. 23, 1979

[30] Foreign Application Priority Data
Feb. 3, 1978 [LU] Luxembourg ............................ 79008

[51] Int. Cl.³ ................. C07C 101/47; A61K 31/195
[52] U.S. Cl. ..................................... 424/319; 562/456; 562/455; 562/457; 562/431; 562/435; 562/426
[58] Field of Search ............... 562/452, 455, 457, 432, 562/455, 456, 426, 435, 431; 424/319, 309

[56] References Cited

U.S. PATENT DOCUMENTS

| | | | |
|---|---|---|---|
| 3,536,753 | 10/1970 | Gruenfeld et al. | 562/456 |
| 3,636,094 | 1/1972 | Yonan | 562/456 |
| 3,839,433 | 10/1972 | Wasley | 562/457 |
| 4,207,341 | 6/1980 | Hubner et al. | 562/457 |
| 4,221,815 | 9/1980 | Weyer et al. | 562/457 |

FOREIGN PATENT DOCUMENTS

| | | | |
|---|---|---|---|
| 2307528 | 11/1976 | France | 562/457 |
| 1082466 | 9/1967 | United Kingdom | 562/457 |

*Primary Examiner*—Natalie Trousof
*Assistant Examiner*—James H. Reamer
*Attorney, Agent, or Firm*—Berman, Aisenberg & Platt

[57] ABSTRACT

The invention relates to ω-[2-(N-lower alkyl-benzamido)-phenyl]-alkanoic acids, their use and preparation, and medicaments containing them.

14 Claims, No Drawings

ω-[2-(N-LOWER ALKYL-BENZAMIDO)-PHENYL]-ALKANOIC ACIDS, THEIR USE, AND MEDICAMENTS CONTAINING THEM

The compounds of the invention are used in the field of pharmacy in medicament form.

O-benzamidophenylalkanoic acids with analgesic and anti-inflammatory effect are described in British Patent Specification 1 082 466. According to D. J. Drain et al. [J. Pharm. Pharmac. 22 (1970) 684–693], o-benzamidophenylpropionic acids possess remarkable anti-inflammatory properties. Surprisingly, it has now been found that N-alkylated o-benzamidophenylalkanoic acids have valuable pharmacological effects which differ distinctly from those of non-N-alkylated compounds.

The invention provides ω-[2-(N-lower alkyl-benzamido)-phenyl]-alkanoic acids of the general formula I

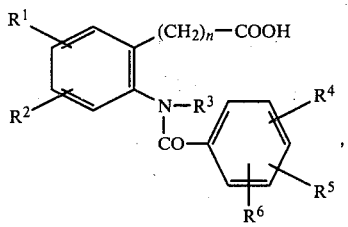
(I)

wherein n denotes a positive whole number from 2 to 5, $R^1$ denotes a hydrogen atom, a halogen atom, a lower alkyl group, a lower alkoxy group, a lower alkylmercapto group, a trifluoromethyl group or a phenyl group which may be substituted by a halogen atom or a lower alkoxy group, $R^2$ denotes a hydrogen atom, a halogen atom, a lower alkyl group or a lower alkoxy group, $R^3$ denotes a lower alkyl group, $R^4$ denotes a hydrogen atom, a halogen atom, a hydroxyl group, a lower alkyl group, a lower alkoxy group, a lower alkylmercapto group, a phenyl group which may be substituted by a halogen atom or a nitro group, a nitro group, an amino group which may be lower alkylated, a lower alkylcarbonyl group, a benzoyl group which may be substituted by a halogen atom, a trifluoromethyl group, a trifluoromethoxy group or a trifluoromethylmercapto group, $R^5$ denotes a hydrogen atom, a halogen atom, a lower alkyl group or a lower alkoxy group, $R^6$ denotes a hydrogen atom, a lower alkyl group or a lower alkoxy group, and their salts with inorganic or organic bases.

Suitable as halogen atoms are fluorine, preferably bromine or chlorine, in particular chlorine. Lower alkyl, lower alkoxy or lower alkylmercapto groups are those which contain 1 to 5 carbon atoms. As lower alkyl groups there are mentioned straight-chain alkyl radicals, such as the methyl, ethyl, propyl, butyl or pentyl radical, of which those with 1 or 2 carbon atoms are preferred, and branched alkyl radicals, such as the isopropyl, isobutyl, sec.-butyl or neopentyl radical, of which those with 4 carbon atoms are preferred. Preferred lower alkoxy or lower alkylmercapto groups are the methoxy or methylmercapto group.

Suitable as salts are those with inorganic or organic bases. Pharmacologically non suitable or incompatible salts are converted according to known-per-se methods into pharmacologically, i.e. biologically, suitable or compatible salts which are preferred among the salts according to the invention. As cations for the salt formation, there are used, inter alia, the cations of the alkali metals, alkaline earth metals or earth metals, but the appropriate cations of organic nitrogen bases, such as amines, aminoalkanols, amino sugars, basic amino acids, are also used.

There are mentioned, for example, the salts of lithium, sodium, potassium, magnesium, calcium, aluminium, ethylenediamine, dimethylamine, diethylamine, morpholine, piperidine, piperazine, N-lower alkyl (e.g. methyl) piperazines, methylcyclohexylamine, benzylamine, ethanolamine, diethanolamine, triethanolamine, tris-(hydroxymethyl)-aminomethane, 2-amino-2-methylpropanol, 2-amino-2-methyl-1,3-propanediol, glucamine, N-methylglucamine, glucosamine, N-methylglucosamine, lysine, ornithine, arginine.

One embodiment of the compounds according to the invention is ω[2-(N-lower alkyl-benzamido)-phenyl]-alkanoic acids of the general formula I*

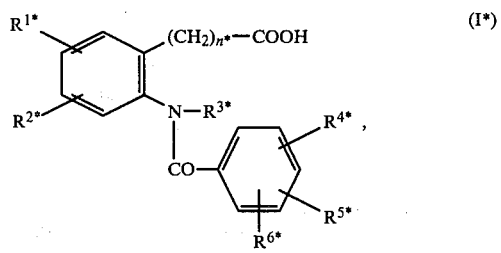
(I*)

wherein n* denotes a positive whole number from 2 to 5, $R^{1*}$ denotes a hydrogen atom, a chlorine atom, a bromine atom, a lower alkyl group, a methoxy group or a phenyl group, $R^{2*}$ denotes a hydrogen atom, a chlorine atom, a bromine atom, a methyl group or a methoxy group, $R^{3*}$ denotes a straight-chain lower alkyl group, $R^{4*}$ denotes a hydrogen atom, a fluorine atom, a chlorine atom, a bromine atom, a lower alkyl group, a hydroxyl group, a lower alkoxy group, a phenyl group, a nitro group, an amino group, a dimethylamino group or a trifluoromethyl group, $R^{5*}$ denotes a hydrogen atom, a chlorine atom, a lower alkyl group or a lower alkoxy group, $R^{6*}$ denotes a hydrogen atom, a lower alkyl group or a lower alkoxy group, and their salts with inorganic or organic bases.

A further embodiment of the compounds according to the invention are those of the general formula I**

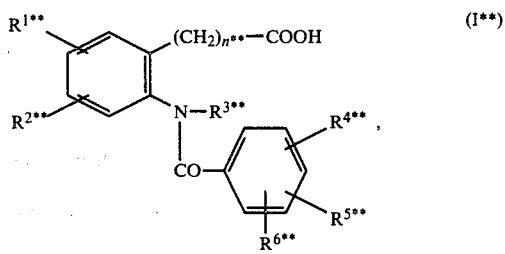
(I**)

wherein n** denotes a positive whole number from 2 to 5,

R¹ denotes a hyrogen atom, a methyl group, a methoxy group, a chlorine atom, a bromine atom or a phenyl group, R² denotes a hydrogen atom, a chlorine atom or a methyl group, R³ denotes a straight-chain alkyl group with 1 to 4 carbon atoms, R⁴ denotes a hydrogen atom, a chlorine atom, a bromine atom, a methyl group, a lower alkoxy group, a phenyl group or a trifluoromethyl group, R⁵ denotes a hydrogen atom, a chlorine atom, a lower alkyl group or a methoxy group, R⁶ denotes a hydrogen atom, a lower alkyl group or a methoxy group, and their salts with inorganic or organic bases.

Preferred compounds according to the invention are those of the general formula I***

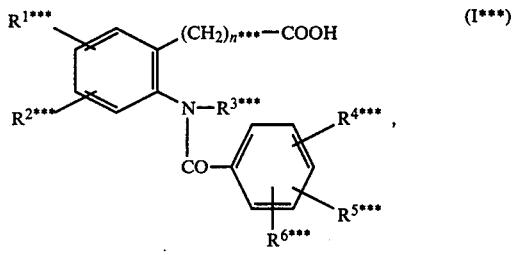

wherein n*** denotes 2 or 3,

R¹* denotes a hydrogen atom, a chlorine atom, a methyl group or a methoxy group, R²* denotes a hydrogen atom or a methyl group, R³* denotes a methyl group or an ethyl group, R⁴* denotes a hydrogen atom, a chlorine atom, a phenyl group or a trifluoromethyl group, R⁵* denotes a hydrogen atom or a chlorine atom, R⁶* denotes a hydrogen atom, and their pharmacologically compatible salts with inorganic or organic bases.

Particularly preferred compounds according to the invention are those of the general formula I****

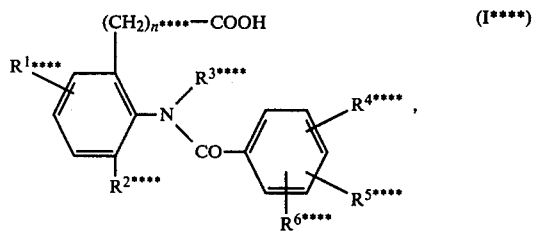

wherein n**** denotes 2 or 3,

R¹**denotes a hydrogen atom, a chlorine atom, a methyl group or a methoxy group, R² denotes a hydrogen atom, R³ denotes a methyl group, R⁴ denotes a hydrogen atom, a chlorine atom or a trifluoromethyl group, R⁵ denotes a hydrogen atom or a chlorine atom, R⁶** denotes a hydrogen atom, and their pharmacologically compatible salts with inorganic or organic bases.

As examples of compounds according to the invention, the following acids and salts are mentioned:

3-[5-bromo-2-(N-ethyl-2,4-dichlorobenzamido)-phenyl]-propionic acid,

3-[2-(N-n-propyl-4-methoxybenzamido)-6-trifluoromethylphenyl]-propionic acid,

3-[5-n-butyl-2-(N-n-butyl-4-nitrobenzamido)-phenyl]-propionic acid,

3-[6-ethyl-2-(N-ethyl-2-phenylbenzamido)-phenyl]-propionic acid,

3-[6-methylmercapto-2-(N-methyl-3,4,5-trimethoxybenzamido)-phenyl]-propionic acid, 4-[4-methyl-2-(N-n-butyl-4-methylmercapto-benzamido)-phenyl]-butyric acid, 4-[2-(N-n-propyl-3-trifluoromethylbenzamido)-phenyl]-butyric acid, 4-[2-(N-n-butyl-4-phenylbenzamido)-phenyl]-butyric acid, 4-[2-(N-methyl-4-acetylbenzamido)-5-methoxyphenyl]-butyric acid, 4-[2-(N-n-pentyl-2-methyl-3-nitrobenzamido)-phenyl]-butyric acid, 4-[2-(N-ethyl-2,4,5-trimethylbenzamido)-phenyl]-butyric acid, triethanolammonium-4-[2-(N-methyl-2,4-dichlorobenzamido)-phenyl]-butyrate.

As compounds according to the invention which are distinguished by particularly interesting effects, there are mentioned 3-[2-(N-methyl-4-chloro-benzamido)-phenyl]-propionic acid, 3-[2-(N-methyl-3,4-dichloro-benzamido)-phenyl]-propionic acid, 4-[2-(N-methyl-4-chloro-benzamido)-6-methoxyphenyl]-butyric acid, 4-[2-(N-methyl-3,4-dichloro-benzamido)-5-methoxyphenyl]-butyric acid, 5-[2-(N-methyl-3,4-dichloro-benzamido)-phenyl]-valeric acid, particularly 3-[2-(N-methyl-benzamido)-phenyl]-propionic acid, 4-[2-(N-methyl-4-chloro-benzamido)-phenyl]-butyric acid, 4-[2-(N-methyl-2,4-dichloro-benzamido)-phenyl]-butyric acid, 3-[2-(N-methyl-3,4-dichloro-benzamido)-5-chlorophenyl]-propionic acid, 3-[2-(N-methyl-3-trifluoromethylbenzamido)-5-chlorophenyl]-propionic acid, 4-[2-(N-methyl-3,4-dichloro-benzamido)-phenyl]-butyric acid, 4-[2-(N-methyl-3-trifluoromethylbenzamido)-phenyl]-butyric acid, 4-[2-(N-methyl-benzamido)-phenyl]-butyric acid, and their pharmacologically compatible salts.

The compounds according to the invention have valuable pharmacological properties which render them commercially exploitable. They have a hypoglycaemic effect and inhibit the glucose formation in the liver.

By reason of their advantageous effectiveness, the ω-[2-(N-lower alkyl-benzamido)-phenyl]-alkanoic acids I, their salts or their embodiments I*, I, I* and I**** are suitable for the treatment and prophylaxis of diseases which are based on disturbances of glucose metabolism. Treated for example are pre-diabetic conditions for the prevention of manifestation of diabetes, manifest diabetes, e.g. adult diabetes, labile diabetes of juveniles. Further, the compounds according to the invention are used for the prophylaxis of coronary, cerebral and peripheral circulation disturbances, diabetic angiopathy or retinopathy.

The invention also relates to a method for combatting the stated diseases through application of the compounds according to the invention. The invention moreover also relates to the use of the compounds according to the invention in combatting the stated diseases.

The invention further provides medicaments which contain one or more of the ω-[2-(N-lower alkyl-benzamido)-phenyl]-alkanoic acids of the general formula I

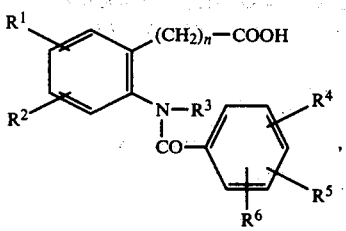

wherein n denotes a positive whole number from 2 to 5, $R^1$ denotes a hydrogen atom, a halogen atom, a lower alkyl group, a lower alkoxy group, a lower alkylmercapto group, a trifluoromethyl group or a phenyl group which may be substituted by a halogen atom or a lower alkoxy group, $R^2$ denotes a hydrogen atom, a halogen atom, a lower alkyl group or a lower alkoxy group, $R^3$ denotes a lower alkyl group, $R^4$ denotes a hydrogen atom, a halogen atom, a hydroxyl group, a lower alkyl group, a lower alkoxy group, a lower alkylmercapto group, a phenyl group which may be substituted by a halogen atom or a nitro group, a nitro group, an amino group which may be lower alkylated, a lower alkylcarbonyl group, a benzoyl group which may be substituted by a halogen atom, a trifluoromethyl group, a trifluoromethoxy group or a trifluoromethylmercapto group, $R^5$ denotes a hydrogen atom, a halogen atom, a lower alkyl group or a lower alkoxy group, $R^6$ denotes a hydrogen atom, a lower alkyl group or a lower alkoxy group, and/or their pharmacologically compatible salts with inorganic or organic bases.

Embodiments of the medicaments are those which contain ω-[2-(N-lower alkyl-benzamido)-phenyl]-alkanoic acids of the formulae I*, I, I*, I**** or their preferred representatives and/or their pharmacologically compatible salts with inorganic or organic bases.

The medicaments are prepared according to processes known per se. As medicaments, the new compounds may be used as such or, where appropriate, in combination with suitable pharmaceutical excipients. If the new pharmaceutical preparations contain, besides the active substances, pharmaceutical excipients, the active substance content of these mixtures is 1 to 95, preferably 15 to 85, percent by weight of the total mixture.

In agreement with the invention, in the human medical field the active substances may be applied in any desired form, e.g. systemically, with the proviso that the formation or maintances of sufficient levels of active substance in the blood or tissues is ensured. That can be achieved for example through oral or parenteral administration in suitable doses. Advantageously, the pharmaceutical preparation of the active substance is present in the form of unit doses which are matched to the desired administration. A unit dose may for example be a tablet, a dragee, a capsule, a suppository or a measured volume amount of a powder, granulate, solution, emulsion or suspension.

By "unit dose" in the sense of the present invention is understood a physically determined unit which contains an individual amount of the active constituent in combination with a pharmaceutical excipient and whose active substance content corresponds to a fraction or multiple of a therapeutic individual dose. An individual dose contains preferably the amount of active substance which is administered in one application and which usually corresponds to a whole, a half, a third or a quarter of the daily dose. If, for an individual therapeutic administration, only a fraction, such as the half or a quarter, of the unit dose is needed, the unit dose is advantageously divisible, e.g. in the form of a tablet with a break score.

The pharmaceutical preparations according to the invention contain, when they are present in unit doses and are intended for application e.g. to humans, 10 to 1000 mg, advantageously 50 to 500 mg and, in particular, 100 to 300 mg, of active substance.

In general it has, in human medicine, proved advantageous, in order to achieve the desired results, to administer the active substance(s), in the case of oral administration, in a daily dose of 0.3 to 150, preferably 1.5 to 75, in particular 3 to 15 mg/kg body weight, where appropriate in the form of several, preferably 1 to 3, individual administrations. An individual administration contains the active substance(s) in amounts of 0.1 to 50, preferably 0.5 to 25, in particular 1 to 5 mg/kg body weight.

In the case of a parenteral treatment, e.g. an intravenous or intramuscular application, similar dosages may be applied. In this therapy, 1 to 5 mg of active substance/kg body weight are applied.

In the case of long-term medication, the therapeutic administration of the pharmaceutical preparation is in general effected at fixed points in time, such as 1 to 4 times daily, e.g. in each case after meals and/or in the evening. In the case of acute occasions, the medication is effected at varying points in time. Under certain circumstances it may be necessary to deviate from the said dosages, depending on the nature, the body weight and the age of the subject to be treated, the nature and the severity of the disease, the nature of the preparation and the application of the medicament as well as the space in time or interval within which the administration is effected. Thus, in some cases it may suffice to manage with less than the above-mentioned amount of active substance whereas in other cases the above-mentioned amount of active substance must be exceeded. The fixing of the respectively necessary optimum dose and type of application of the active substances is effected by the skilled man on the basis of his specialised knowledge.

The pharmaceutical preparations consist as a rule of the active substances according to the invention and non-toxic, pharmaceutically compatible medicament excipients which are used as admixture or diluent in solid, semi-solid or liquid form or as surrounding agent, for example in the form of a capsule, a tablet coating, a bag or other container, for the therapeutically active constituent. An excipient may serve e.g. as agent for the absorption of the medicament by the body, as formulation auxiliary, as sweetener, as taste corrector, as dyestuff or as preservative.

For oral application there may be used e.g. tablets, dragees, hard and soft capsules, e.g. of gelatin, dispersible powders, granulates, aqueous and oily suspensions, emulsions, solutions or syrups.

Tablets may contain inert diluents, e.g. calcium carbonate, calcium phosphate, sodium phosphate or xylitol; granulation or distribution agents, e.g. calcium phosphate or alginates; binders, e.g. starch, gelatin or acacia gum; and glidants, e.g. aluminium stearate or magnesium stearate, talc or silicone oil. They may additionally be provided with a coating which may also be of such a nature that it causes a delayed dissolving and absorption of the medicament in the gastro-intestinal tract and thus e.g. a better tolerance, protraction or a retardation is achieved. Gelatin capsules may contain the medicament mixed with a solid diluent, e.g. calcium carbonate or kaolin, or an oily diluent, e.g. paraffin oil.

Aqueous suspensions may contain suspending agents, e.g. sodium carboxymethyl cellulose, methyl cellulose, hydroxypropyl cellulose, sodium alginate, polyvinylpyrrolidone, gum tragacanth or acacia gum; dispersing and wetting agents, e.g. polyoxyethylene stearate, heptadecaethyleneoxycetanol, polyoxyethylene sorbitol mono-oleate, polyoxyethylene sorbitan mono-oleate or lecithin; preservatives, e.g. methyl or propyl hydroxybenzoates; flavouring agents; sweetners, e.g. saccharin, sodium cyclamate.

Oily suspensions may contain e.g. paraffin oil and thickeners, such as beeswax, hard paraffin or cetyl alcohol; further, sweeteners, flavouring and anti-oxidants.

Water-dispersible powders and granulates may contain the medicaments in admixture with dispersing, wetting and suspending agents, e.g. those mentioned above, and with sweeteners, flavourings and colouring matters.

Emulsions may contain e.g. paraffin oil besides emulsifying agents, such as acacia gum, gum tragacanth, phosphatides, sorbitan mono-oleate, polyoxyethylene sorbitan mono-oleate, and sweeteners and flavourings.

For the parenteral application of the medicaments, one may use sterile-injectable aqueous suspensions, isotonic salt solutions or other solutions which may contain the dispersing or wetting agents and/or pharmacologically compatible diluents, e.g. propylene glycol or butylene glycol.

The active substance(s) may, where appropriate, also be formulated with one or more of the stated excipients or additives in micro-encapsulated form.

Besides the ω-[2-(N-lower alkyl-benzamido)-phenyl]-alkanoic acids according to the invention, in which the substituents have the same meaning as above and/or their salts the pharmaceutical preparations may also contain one or more pharmacologically active constituents of other medicament groups, such as anti-diabetes agents (sulphonamides, sulphonylureas, inter alia), e.g. carbutamide, tolbutamide, chlorpropamide, glibenclamide, glibornuride, glisoxepide, gliquidone, glymidine or hypolipidaemic agents, such as nicotinic acid and their derivatives and salts.

The invention also provides a process for the preparation of the ω-[2-(N-lower alkyl-benzamido)-phenyl]-alkanoic acids of the general formula I or of the embodiments I*, I, I*, I**** and their salts with inorganic or organic bases. The process is characterized in that (a) a ω-(2-lower alkylamino-phenyl)-alkanoic acid of the general formula II

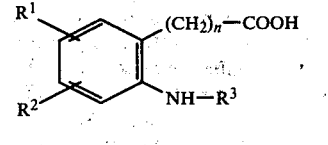

wherein n, $R^1$, $R^2$ and $R^3$ have the meaning stated above, or a salt thereof, is acylated in basic solution with a benzoyl derivative of the general formula III

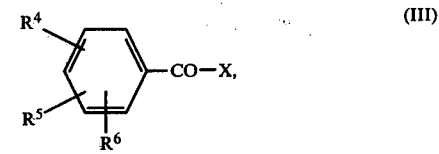

wherein

X denotes a halogen atom and $R^4$, $R^5$ and $R^6$ have the meaning stated above, and, if desired, obtained free acids are subsequently converted into their salts, or obtained salts are subsequently converted into the free acids, or (b) a ω-[2-(N-lower alkyl-benzamido)-phenyl]-alkyl-compound of the general formula IV

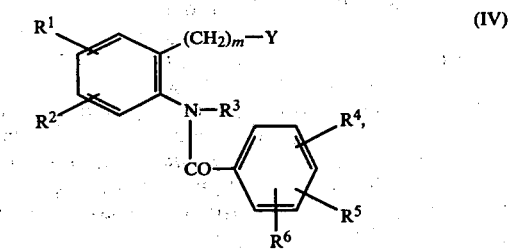

wherein $R^1$, $R^2$, $R^3$, $R^4$, $R^5$ and $R^6$ have the meaning stated above, m is a positive whole number from 1 to 4 and Y is a leaving group, is reacted with a dialkyl malonate, preferably with a di-lower-alkyl malonate, in the presence of basic condensation agents, and the resulting substituted malonic ester is saponificated and decarboxylated, and, if desired, obtained free acids are subsequently converted into their salts, or obtained salts are subsequently converted into the free acids, or (c) in order to prepare compounds of the formula I, wherein n=2, a 2-(N-lower alkyl-benzamido)-cinnamic acid of the general formula V

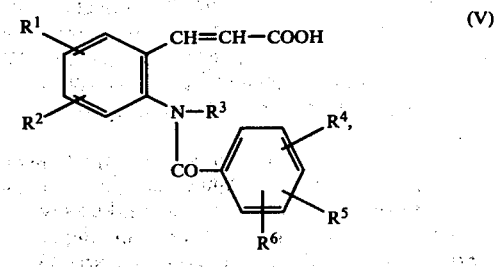

wherein

R¹, R², R³, R⁴, R⁵ and R⁶ have the meaning stated above, or a salt or a lower alkyl ester thereof, is hydrogenated and, where appropriate, ω-[2-(N-lower alkylbenzamido)phenyl]-propionic acid lower alkyl esters obtained subsequently are converted into the free acids or their salts.

The acylation according to process variant a) is carried out according to methods known per se. It is effected for example by providing the aqueous basic solution of the freshly prepared starting compounds II and adding the benzoyl derivatives III. This, however, does not exclude the possibility that there may also be added other solvents or solubilisers, such as ethers, e.g. diethyl ether or tetrahydrofuran or diethers of polyols, e.g. dioxan or diglyme, or ketones, e.g. acetone, or amides, e.g. dimethylformamide, or possibly halogenated hydrocarbons, e.g. methylene chloride, benzene, toluene, cyclohexane, petroleum ether, or further aprotic solvents such as dimethyl sulphoxide or acetonitrile. Further, the acids II, preferably in the form of a salt, may also be suspended in non-aqueous solvents, e.g. ethers, ketones, amides or possibly halogenated hydrocarbons, and reacted, in the presence of bases, with the benzoyl derivatives III, preferably the benzoyl chlorides.

Basic solutions are prepared predominantly with the use of alkalis, e.g. lithium hydroxide, sodium hydroxide or potassium hydroxide, sodium hydrogen carbonate, sodium or potassium carbonate. However, there may additionally be used the appropriate alkaline earth metal compounds, e.g. calcium or barium hydroxide, or organic bases, such as tetramethylammonium hydroxide. The base used must be suitable to adjust the pH value of the solution to 7.2 to 10, preferably 8 to 9, in order to avoid undesired side-reactions; otherwise, the nature of the base used is of lesser importance. Although the basic solutions are in general supplied immediately to the acylation, if required they may, e.g. for the production of storage solutions, be prepared some considerable length of time before the acylation.

The reaction times and temperatures lie in the range of 0.5 to 10 hours and 0° to 40° C.; when the reaction is carried out at room temperature, it is complete in general within 1 to 2 hours.

The reaction according to process variant (b) is carried out according to methods known per se. Usual leaving groups in nucleophilic substitution, such as halogen atoms, e.g. a chlorine or a bromine atom, or alkylsulphonyloxy or benzenesulphonyloxy groups, such as a mesyloxy or a p-tolylsulphonyloxy group, are appropriate leaving groups Y. The reaction of the compounds IV with the dialkyl malonates is carried out according to the usual malonic ester synthesis; as for example, the compounds IV are reacted with the anion of a dialkyl malonate in anhydrous solvents, such as lower alkanols (preferably ethanol), amides, optionally halogenated hydrocarbons, ketones, ethers, dimethylsulphoxide, or acetonitrile. The anion of the dialkyl malonate is prepared preferably in situ, e.g. from sodium ethanolate and diethyl malonate. It may be used, however, also in the form of a previously prepared alkaline metal salt, e.g. as sodium malonic ester. The resulting substituted malonic ester is saponificated in usual manner, e.g. with alcoholic potassium hydroxide. The free dicarboxylic acid thus prepared is decarboxylated according to known methods, e.g. by heating up to temperatures of 150° to 200° C. Saponification and decarboxylation are carried out normally in two steps. However, this does not exclude a realization in a single vessel method.

The hydrogenation according to process variant c) is carried out according to methods known per se. It is effected for example by hydrogenation of an appropriate cinnamate in the presence of a palladium charcoal catalyst and subsequent hydrolysis of the ester to the corresponding propionic acid (see Organic Synthesis, Coll. Vol. IV, 408). In a similar manner a cinnamic acid V is reduced in weakly alkaline solution with hydrazine in the presence of catalytic amounts of Raney Nickel [N. S. Hjelte, Chem. Scand. 15 (1961) 1200]. Alternatively, in the hydrogenation an appropriate cinnamic acid alkali metal salt in aqueous-basic solution with sodium amalgam is used according to E. Fischer [in Fieser/Fieser, Reagents for Organic Synthesas, Vol. 1, p. 1031. Wiley and Sons, New York (1967)]. The same salts are also converted to the compounds I according to the invention by electrolytic reduction (see Organic Synthesis, Coll. Vol. I, 311). In the hydrogenation, there are expediently used only those starting compounds V whose substituents are not attacked by the hydrogenation, for example nitro groups are reduced during hydrogenation.

The conversion of the free acids into the salts or of the salts into the free acids is effected according to methods known to the man skilled in the art. Salts may for example be obtained by reacting free acids of the general formula I or the embodiments I*, I, I* or I**** with the stoichiometric equivalent of an appropriate base or converting readily soluble salts into sparingly soluble salts through double decomposition or converting any desired salts into pharmacologically compatible salts. Free acids I are obtained through reaction of the salts with mineral acids, e.g. hydrochloric acid, and working up.

The phenylalkanoic acids II to be used for the process (a) according to the invention are obtained through basis hydrolysis of the appropriate N-lower alkyl-lactams X in aqueous or non-aqueous media, which lactams X are accessible through alkylation of the appropriate lactams IX with alkylating agents R³-Z. The tetra-hydroquinolin-2-ones (IX, n=2) required for the preparation of the phenylalkanoic acids II (wherein n=2) are obtained through Friedel-Crafts alkylation of appropriate β-chloropropionanilides (VI).

The 2-aza-benzo-[c]-cycloheptanones (IX, n=3) or -cyclooctanones (IX, n=4) or -cyclononanones (IX, n=5) required for the preparation of the phenylalkanoic acids II (wherein n=3, 4 or 5) are prepared by ring expansion of appropriate benzo-[b]-cyclohexanones (VII, n=3) or -cycloheptanones (VII, n=4) or -cyclooctanones (VII, n=5), e.g. with the assistance of the Schmidt reaction (with sodium azide) or through Beckman rearrangement (of the corresponding ketoximes VIII). There results the following reaction scheme:

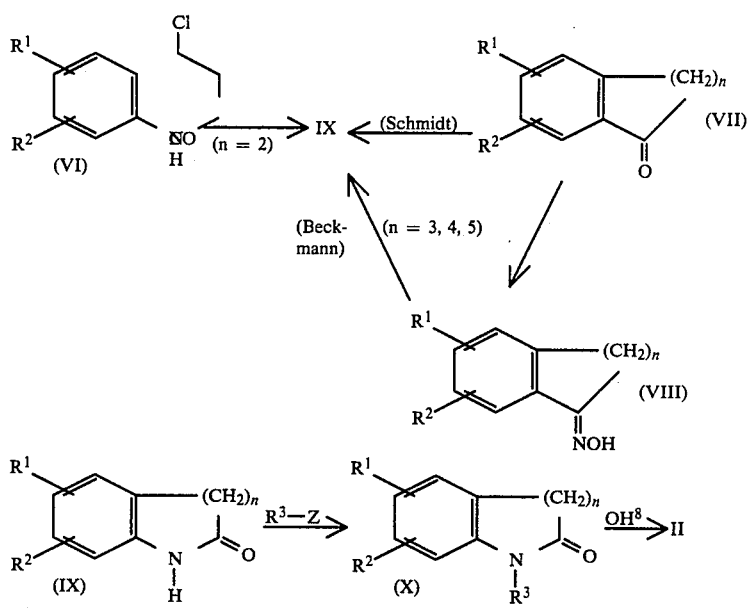

Alternatively the phenylalkanoic acids II (n=3, 4 or 5) are produced by reaction of optionally substituted 2-nitrotoluenes XI with a lithium base, e.g. n-butyllithium, subsequent reaction with a ω-haloalkane carboxylic acid lower alkyl ester XII, wherein Hal is a chlorine or a bromine atom and $R^7$ denotes a lower alkyl group, catalytic hydrogenation of the product XIII (transformation of the nitro group into an amino group) and following alkylation according to known methods. During alkylation the ester group is saponificated; one obtains a solution of II, which can be used immediately for further reactions.

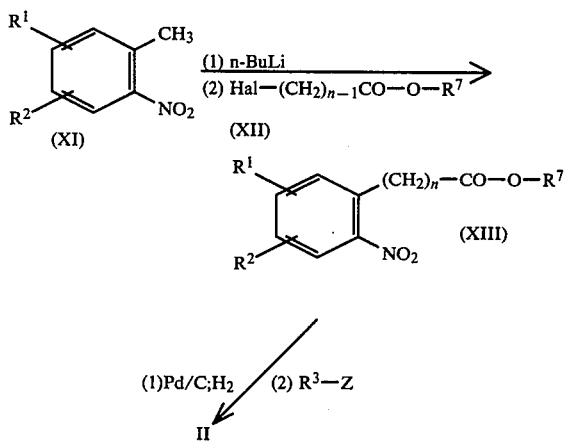

The Friedel-Crafts alkylation of the β-chloropropionanilides VI or the ring expansion of the benzocycloalkanones VII to the lactams IX is effected according to known processes. For alkylation, the lactams IX are reacted, either under moisture exclusion in inert solvents, such as ethers, dimethylformamide, toluene, with sodium amide or sodium hydride, or with sodium hydroxide solution and subsequently with the usual alkylating agents $R^3$—Z, wherein $R^3$ denotes a lower alkyl group and Z denotes a leaving group. As alkylating agents there are mentioned, among other things, methyl iodide, dimethyl sulphate, ethyl iodide, propyl bromide, isobutyl bromide, neopentyl iodide. The N-lower alkyl-lactams X are converted into the starting compounds II through vigorous heating in basic solution (temperatures from 100° C. to 160° C., where appropriate with use of an autoclave). Expediently, the compounds II are, after removal of excess solvent, further reacted, without isolation, with the benzoyl derivatives III to give the compounds according to the invention, since undesired yield losses are avoided in this way. Further, the basic solutions used for the hydrolysis of the N-lower alkyl-lactams X may serve simultaneously for the neutralisation of the hydrogen halides liberated during the acylation.

The invention therefore also provides a process for the preparation of the compounds I and their salts which is characterised in that a N-lower alkyl-lactam X is hydrolysed in basic solution and acylated with a benzoyl derivative III and, if desired the free acid obtained is converted into a salt or a salt obtained is converted into the free acid.

This advantageous embodiment, however, does not exclude that, if desired, the ω-(2-lower alkylaminophenyl)-alkanoic acids II, after hydrolysis, are isolated in the form of the salts and acylated in a separate step; where appropriate, other basic solutions may be used.

In order to prepare the compounds of the embodiments I*, I, I* or I****, appropriate starting materials II*, II, II* or II****, III*, III, III* or III****, IV*, IV, IV* or IV****, V*, V, V* or V**** or X*, X, X* or X**** wherein the substituents have the meaning stated above, are reacted.

The benzoyl derivatives III which may be used for the process according to the invention are known to the man skilled in the art or may be prepared according to known processes. Among the acid halides III, the chlorides are preferred. The starting compounds V and the initial products are likewise known or may be prepared according to known processes. The starting compounds IV for the process variant (b) are also obtained according to known processes. Thus they are prepared from alkanoic acids I, which are prepared by process variant (a) or (c), by reduction of the —COOH-group to the —CH$_2$—OH—group and subsequent transformation into the CH$_2$-Y-group (e.g. by halogenation or tosylation).

The following Examples serve for illustrating the invention. Temperatures are in °C., m.p. denotes melting point, b.p. denotes boiling point (at ... mm Hg).

EXAMPLES

EXAMPLE 1

3-[2-(N-methylbenzamido)-phenyl]-propionic acid

R$^3$=—CH$_3$, R$^1$=R$^2$=R$^4$=R$^5$=R$^6$=—H, n=2

(a) An aqueous-basic solution, freshly prepared according to (b), of 3-[2-(N-methylamino)-phenyl]-propionic acid is adjusted to pH 8.5 with 2 N hydrochloric acid. A solution of 9.0 g of benzoyl chloride in 50 ml of diethyl ether is added dropwise, with stirring; the pH of the reaction mixture is kept constant at 8.5 through addition of 1 N sodium hydroxide solution. After a further hour's stirring, the aqueous phase is separated off and washed twice with, in each case, 100 ml of diethyl ether. Acidification to pH 1-2 is then effected with 2 N hydrochloric acid, followed by extraction with methylene chloride (5 times, with 200 ml each time). The extracts are dried over sodium sulphate and evaporated. The residue is recrystallized from ethyl acetate and yields 11.9 g (66% of theory) of the title compound, m.p. 106°-107° C.

(b) 10.4 g of N-methyl-1,2,3,4-tetrahydroquinolin-2-one with 12.2 g of potassium hydroxide in 45 ml of ethyleneglycolmonoethyl ether are heated to reflux for 3.5 hours. After cooling, dilution is effected with 400 ml of water, followed by extraction twice with, in each case, 200 ml of diethyl ether. The organic extracts are discarded. The freshly prepared solution is used under (a), without further working up.

EXAMPLE 2

3-[2-(N-methyl-3,4-dichlorobenzamido)-phenyl]-propionic acid

R$^3$=—CH$_3$, R$^4$=R$^5$=—Cl, R$^1$=R$^2$=R$^6$=—H, n=2

(a) To a solution, obtained according to (b), of 3-[2-(N-methylamino)phenyl]-propionic acid there is added dropwise, with stirring, a solution of 13.4 g of 3,4-dichlorobenzoyl chloride in 50 ml of diethyl ether; the pH is kept constant at 8.5 through addition of 1 N sodium hydroxide solution. Further working up as in Example 1 (a) leads to 14.3 g (63% of theory) of the title compound, m.p. 149°-150° C.

(b) 10.4 g of N-methyl-1,2,3,4-tetrahydroquinolin-2-one together with 16.6 g of barium hydroxide and 200 ml of water are heated to 150° for 16 hours in a stirred autoclave. After cooling, water (400 ml) is added and excess barium salt is precipitated with carbon dioxide; the pH must not fall below 7.5. The precipitate is filtered off; 10% strength sodium carbonate solution is added to the filtrate until pH 8.5 is reached. After renewed filtration, the solution, without further working up, is used under (a).

N-methyl-1,2,3,4-tetrahydroquinolin-2-one is obtained as viscous oil through N-methylation of 1,2,3,4-tetrahydroquinolin-2-one with dimethyl sulphate analogously to Example 3 b).

EXAMPLE 3

3-[5-chloro-2-(N-methyl-2-phenylbenzamido)-phenyl]-propionic acid

R$^1$=—Cl, R$^3$=—CH$_3$, R$^4$=phenyl, R$^2$=R$^5$=R$^6$=—H, n=2

(a) The aqueous-basic solution, prepared according to b), of 3-(5-chloro-2-methylamino-phenyl)-propionic acid is adjusted to pH 8.5 analogously to Example 1 (a) and reacted with 6.6 g of 2-phenylbenzoyl chloride and worked up. Recrystallisation from ethyl acetate yields 7.1 g (56% of theory) of the title compound:

(b) 17.6 g of 3-chloropropion-4-chloranilide together with 32.4 g of aluminium chloride are heated to 110° for 3 hours. The still hot liquid is stirred with 600 ml of ice water. After 20 ml of 2 N hydrochloric acid have been added, extraction is effected three times with, in each case, 200 ml of ethyl acetate. Drying of the organic phase over sodium sulphate, concentration and recrystallisation from ethyl acetate/petroleum ether (1:1) yields 10.2 g (70% of theory) of 6-chloro-1,2,3,4-tetrahydroquinolin-2-one, m.p. 165°-167° C.

This tetrahydroquinolinone is dissolved in 100 ml of dimethylformamide/toluene (1:1); after addition of 1.8 g of sodium hydride (80% in paraffin oil), stirring is effected for 30 minutes at room temperature, followed by addition of 7.8 g of dimethyl sulphate and heating to 50° for 1 hour. After cooling of the mixture, 600 ml of water and 20 ml of 2 N sodium hydroxide solution are added; stirring is effected for 10 minutes, followed by acidification with 2 N hydrochloric acid. Extraction with ethyl acetate (4 times, with 300 ml each time), drying and concentration yield a solid residue which is recrystallised from ethyl acetate/petroleum ether (1:1) and yields 6.0 g (55% of theory) of 6-chloro-1-methyl-1,2,3,4-tetrahydroquinolin-2-one (m.p. 76°-78° C.).

6.0 g of 6-chloro-1-methyl-1,2,3,4-tetrahydroquinolin-2-one are hydrolysed analogously to Example 1 (b). The solution so prepared is worked up analogously to 1 (b) and then further reacted under (a).

EXAMPLE 4

4-[2-(N-methyl-4-chlorobenzamido)-phenyl]-butyric acid

R$^3$=—CH$_3$, R$^4$=—Cl, R$^1$=R$^2$=R$^5$=R$^6$=—H, n=3

(a) The aqueous-basic solution, obtained according to (b), of 4-(2-N-methylamino-phenyl)-butyric acid is, analogously to Example 1 (a), acylated with 6.3 g of 4-chlorobenzoyl chloride in 30 ml of diethyl ether and worked up. After recrystallisation from ethyl acetate/petroleum ether (1:1), there are obtained 6.1 g (51% of theory) of the title compound, m.p. 123°-123° C.

(b) 30.0 g of α-tetralonoxime are dissolved in 100 ml of pyridine, and 100 ml of phosphorus oxychloride in 250 ml of pyridine are slowly added, with ice cooling. Stirring is effected at 0° for 2 hours, then the solution is diluted with 300 ml of chloroform. The mixture is cautiously poured on to 1 kg of ice and 400 ml of concentrated hydrochloric acid (violent reaction!). After stirring until completion of the reaction, the organic phase is separated off. The aqueous phase is extracted with 3 times 300 ml of chloroform; the united extracts are dried over sodium sulphate, concentrated and recrystallised from ethanol. Yield 17.4 g (59% of theory) of 2-aza-benzo[c]-cycloheptanone (m.p. 141°-142° C.).

This cycloheptanone is N-methylated analogously to Example 3 (b) with sodium hydride and dimethyl sulphate and, after working up and recrystallisation from ethyl acetate/petroleum ether (1:3), yields 17.3 g (92% of theory) of 2-aza-2-methyl-benzo[c]-cycloheptanone.

6.3 g of 2-aza-2-methyl-benzo[c]-cycloheptanone are hydrolysed analogously to Example 1 (b) with 8.1 g of potassium hydroxide in 40 ml of ethyleneglycolmonoethyl ether, worked up (i.e. freed from ethyleneglycolmonoethyl ether) and then used for the reaction according to (a).

EXAMPLE 5

3-[2-(N-methyl-4-chlorobenzamido)-phenyl]-propionic acid $R^3 = -CH_3$, $R^4 = -Cl$, $R^1 = R^2 = R^5 = R^6 = -H$, $n = 2$ Analogously to Example 1 (a), an aqueous-basic solution of 6.5 g of potassium 3-[2-(N-methylamino)-phenyl]-propionate is acylated with 4-chlorobenzoyl chloride. After working up and recrystallisation from ethyl acetate there are obtained 5.3 g (56% of theory) of the title compound (m.p. 156°–158° C.).

EXAMPLE 6

4-[2-(N-methylbenzamido)-phenyl]-butyric acid $R^3 = -CH_3$, $R^1 = R^2 = R^4 = R^5 = R^6 = -H$, $n = 3$ (a) The aqueous-basic solution, prepared according to (b), of 4-(2-methylamino-phenyl)-butyric acid is diluted with 200 ml of water and adjusted to pH 8.5 with 2 N hydrochloric acid. Analogously to Example 4 (a), benzoyl chloride is added dropwise and pH 8.5 is kept through addition of sodium hydroxide solution. Recrystallisation from ethyl acetate/petroleum ether (1:2) yields 7.3 g (48% of theory) of the title compound (m.p. 101° C.).

(b) 9.0 g of 2-aza-2-methyl-benzo[c]-cycloheptanone in 200 ml of 6 N sodium hydroxide solution are heated under reflux for 60 hours; after cooling, washing is effected with twice 150 ml of diethyl ether. The solution so prepared is further reacted under (a).

EXAMPLE 7

4-[2-(N-methyl-3-trifluoromethylbenzamido)-phenyl]-butyric acid $R^3 = -CH_3$, $R^4 = -CF_3$, $R^1 = R^2 = R^5 = R^6 = -H$, $n = 3$ Analogously to Example 6 (b) and (a), 4.5 g of 2-aza-2-methylbenzo[c]-cycloheptanone are hydrolysed in 6 N sodium hydroxide solution and subsequently acylated at pH 8.5 with 3-trifluoromethylbenzoyl chloride. After recrystallisation from petroleum ether, there are obtained 2.7 g (30% of theory) of the title compound (m.p. 84°–85° C.).

EXAMPLE 8

4-[2-(N-ethyl-2,4-dichlorobenzamido)-phenyl]-butyric acid $R^3 = -CH_2-CH_3$, $R^4 = R^5 = -Cl$, $R^1 = R^2 = R^6 = -H$, $n = 3$ (a) The residue, prepared according to (b), containing potassium 4-[2-(N-ethylamino)-phenyl]-butyrate is dissolved in 100 ml of water; after adjustment of the pH of the solution to 8.2 (with 2 N hydrochloric acid), 3.5 g of 2,4-dichlorobenzoyl chloride in 50 ml of diethyl ether are added dropwise. Through simultaneous addition of 1 N sodium hydroxide solution, the pH of the solution is kept constant at 8.2. Working up and recrystallisation from ethyl acetate/petroleum ether (1:1) yield 3.1 g (48% of theory) of the title compound as oil.

(b) 3.1 g of 2-aza-2-ethyl-benzo[c]-cycloheptanone in 20 ml of 5 N potassium hydroxide are heated under reflux for 60 hours. After cooling, the solution is evaporated to dryness; the solid residue, which still contains excess potassium hydroxide, is washed with diethyl ether and, without further purification, used in (a).

EXAMPLE 9

3-[4-chloro-2-(N-methyl-4-chlorobenzamido)-phenyl]-propionic acid $R^3 = -CH_3$, $R^1 = R^4 = -Cl$, $R^2 = R^5 = R^6 = -H$, $n = 2$ Analogously to Example 1 (b) and (a), 5.2 g of 7-chloro-1-methyl-1,2,3,4-tetrahydroquinolin-2-one are hydrolysed and freed from ethyleneglycolmonoethyl ether through washing with diethyl ether. The aqueous-basic solution of 3-(4-chloro-2-methylamino-phenyl)-propionic acid adjusted to pH 8.6 is acylated with 4.6 g of 4-chlorobenzoyl chloride; after appropriate working up, 6.8 g of the title compound are obtained as viscous oil.

EXAMPLE 10

3-[5-chloro-2-(N-methyl-3-trifluoromethylbenzamido)-phenyl]-propionic acid $R^1 = -Cl$, $R^3 = -CH_3$, $R^4 = -CF_3$,
$R^2 = R^5 = R^6 = -H$, $n = 2$ A solution of 6 g of 3-(5-chloro-2-methylamino-phenyl)-propionic acid, prepared according to Example 3 (b), is reacted with 6.2 g of 3-trifluoromethylbenzoyl chloride in 30 ml of dioxane at pH 8.5 and worked up analogously to Example 1 (a). After recrystallisation from ethyl acetate/petroleum ether (1:1) there are obtained 6.4 g (55% of theory) of the title compound, m.p. 124°–126° C.

EXAMPLE 11

3-[5-chloro-2-(N-methyl-3,4-dichlorobenzamido)-phenyl]-propionic acid $R^1 = R^4 = R^5 = -Cl$, $R^3 = -CH_3$, $R^2 = R^6 = -H$, $n = 2$ (a) 6.2 g of methyl 5-chloro-2-(N-methyl-3,4-dichlorobenzamido)-cinnamate, dissolved in 200 ml of ethyl acetate, are hydrogenated after addition of 0.5 g of palladium charcoal catalyst (10% Pd) in a circulation apparatus at normal pressure. After filtration the solvent is removed under a vacuum; the residue is treated with 150 ml of a 5% strength potassium hydroxide solution (in methanol), concentrated after 24 hours and worked up by extraction. One obtains 5.4 g of the title compound, m.p. 159°–160° C.

(b) 12.8 g of methyl 2-acetamido-5-chlorocinnamate are dissolved in 200 ml of dimethylformamide/toluene (1:1), and 1.6 g sodium hydride (80% in paraffin oil) are added. Stirring is effected for 30 minutes, and at 0° 7 g of dimethylsulphate are added drop by drop. After 2 hours additional stirring at room temperature, 500 ml of water and 50 ml of 2 N sodium hydroxide solution are added followed by washing with toluene. After acidification, extraction with methylene chloride, removing of the solvent and chromatografic purification one obtains 7.6 g of 5-chloro-2-(N-methyl-acetamido)-cinnamic acid as oil. This oil is stirred for 24 hours at 100° with 100 ml of 5 N hydrochloric acid; after cooling the pH is adjusted to 8.5 with dilute sodium hydroxide solution, and 10 g of sodium bicarbonate are added. 7.5 g of 3,4-dichlorobenzoyl chloride in 50 ml of toluene are added dropwise. Working up as in Example 1(a) yields 10.8 g of 5-chloro-2-(N-methyl-3,4-dichlorobenzamido)cinnamic acid, which are reacted without further purification for 2 days at room temperature with 200 ml of methanol under addition of 4 ml of concentrated sulphuric acid. Extraction with methylene chloride and working up yield 8.3 g of the corresponding methyl ester, which is reacted analogously to (a).

EXAMPLE 12

Benzylammonium-3-[2-(N-methyl-3,4-dichlorobenzamido)-phenyl]-propionate $R^3 = -CH_3, R^4 = R^5 = -Cl, R^1 = R^2 = R^6 = -H, n = 2$ 2.2 g of 3-[2-(N-methyl-3,4-dichlorobenzamido)-phenyl]-propionic acid are dissolved in 15 ml of diethyl ether and 10 ml of acetone. After addition of 0.8 g of benzylamine and brief stirring, the solution is evaporated. The viscous residue is washed several times with diethyl ether, but resists crystallisation attempts. 2.85 g of the title compound are obtained as solidified oil.

EXAMPLE 13

3-[2-(N-ethyl-3,4-dichlorobenzamido)-5-methyl-phenyl]-propionic acid $R^1 = -CH_3, R^3 = -CH_2-CH_3, R^4 = R^5 = -Cl, R^2 = R^6 = -H, n = 2$ (a) An aqueous-basis solution of 3-(2-ethylamino-5-methyl-phenyl)-propionic acid, prepared analogously to Example 3(b) from 4.7 g of 1-ethyl-6-methyl-1,2,3,4-tetrahydroquinolin-2-one is reacted with 5.2 g of 3,4-dichlorobenzoyl chloride in 30 ml of methylene chloride and worked up according to Example 1(a). After recrystallisation from diethyl ether/petroleum ether (1:3) there are obtained 2.1 g (22% of theory) of the title compound, m.p. 107°–109° C.

(b) 1.4 g of benzyltriethyl ammoniumchloride (TEBA) and a solution of 12 g of sodium hydroxide in 12 ml of water are added with stirring to a solution of 9.6 g of 6-methyl-1,2,3,4-tetrahydroquinolin-2-one in 150 ml of methylene chloride. After 20 minutes 23.2 g of diethyl sulphate are added slowly dropwise; stirring is effected for 20 hours, the last 4 hours under reflux. Excess diethyl sulphate is decomposed by addition of 100 ml of 4 N sodium hydroxide solution. One acidifies and extracts for several times with methylene chloride. The organic phase is dried and concentrated and the residue is purified by chromatography over silica gel (eluent: methylene chloride). 9.4 g (83% of theory) of 1-ethyl-6-methyl-1,2,3,4-tetrahydroquinolin-2-one are obtained as oil.

EXAMPLE 14

Ammonium-3-[5-methyl-2-(N-methyl-3-trifluoromethyl-benzamido)-phenyl]-propionate $R^1 = R^3 = -CH_3, R^4 = -CF_3, R^2 = R^5 = R^6 = -H, n = 2$ (a) An aqueous-basic solution (pH 8.0) of 5.3 g of 3-(2-methylamino-5-methyl-phenyl)-propionic acid prepared according to (b) is evaporated to dryness in vacuo. After azeotropic removal of water traces by evaporation with toluene, the residue is suspended with 150 ml of dimethyl formamide; 2.8 g of triethylamine, and then dropwise with stirring 6.0 g of 3-trifluoromethylbenzoyl chloride are added thereto. After 12 hours of stirring and distribution between water and diethyl ether one works up according to Example 1(a). After precipitation of the crude product with ammonia in isopropanol/diethyl ether (1:10) and recrystallisation one obtains 4.1 g of the title compound, m.p. 82°–85° (decomposition).

(b) Analogously to Example 13(b) of 9.6 g of 6-methyl-1,2,3,4-tetrahydroquinolin-2-one are reacted with TEBA and dimethyl sulphate in methylene chloride/50% strength sodium hydroxide solution. After extraction with methylene chloride there are obtained 10.2 g (98% of theory) of 1,6-dimethyl-1,2,3,4-tetrahydroquinolin-2-one as a tough oil. The oil is hydrolysed in aqueous-basic solution analogously to Example 3(b).

EXAMPLE 15

4-[2-(N-methyl-2,4-dichlorobenzamido)-phenyl]-butyric acid $R^3 = -CH_3, R^4 = R^5 = Cl, R^1 = R^2 = R^6 = -H, n = 3$ 30 g of solid sodium bicarbonate are added to an aqueous-basic solution (pH = 8–9) of 6.3 g of 4-(2-N-methylamino-phenyl)-butyric acid [prepared analogously to Example 4(b)]. One adds dropwise with stirring a solution of 7.5 g of 2,4-dichlorobenzoyl chloride in 50 ml of diethyl ether. 2 hours after addition one works up according to Example 4(a). 1.6 g of the title compound, m.p. 102°–103°, are obtained after recrystallisation from ethyl acetate/petroleum ether (1:4).

EXAMPLE 16

4-[2-(N-methyl-3,4-dichlorobenzamido)-phenyl]-butyric acid $R^3 = -CH_3, R^4 = R^5 = -Cl, R^1 = R^2 = R^6 = -H, n = 3$ 5.2 g of 3,4-dichlorobenzoyl chloride in 50 ml of methylen chloride are added at pH 8.5 [analogously to Example 4(a)] to an aqueous-basic solution of 5.4 g of 4-(2-N-methylamino-phenyl)-butyric acid, prepared according to Example 4(b). Working up and recrystallisation from ethyl acetate/petroleum ether (1:1) yield 5.7 g (63% of theory) of the title compound, m.p. 120°–121° C.

EXAMPLE 17

4-[2-(N-methyl-2-phenyl-benzamido)-phenyl]-butyric acid $R^3 = -CH_3, R^4 = \text{phenyl}, R^1 = R^2 = R^5 = R^6 = -H, n = 3$ 6.3 g of 4-(2-N-methylamino-phenyl)-butyric acid in aqueous-basic solution [see Example 4(b)] are reacted with 7.8 g of biphenyl-2-carboxylic acid chloride. Working up and recrystallisation from ethyl acetate yield 4 g (30% of theory) of the title compound, m.p. 154°–155° C.

EXAMPLE 18

4-[4-methoxy-2-(N-methyl-2,4-dichlorobenzamido)-phenyl]-butyric acid $R^1 = -OCH_3, R^3 = -CH_3, R^4 = R^5 = -Cl, R^2 = R^6 = -H, n = 3$ (a) An aqueous-basic solution prepared according to (b) of 4-(4-methoxy-2-N-methylamino-phenyl)-butyric acid is reacted analogously to Example 1(a) with 6.7 g of 2,4-dichlorobenzoyl chloride and worked up. Recrystallisation of the crude product from ethyl acetate/- petroleum ether (1:1) yields 4.8 g (38% of theory) of the title compound, m.p. 90°–91° C.

(b) Schmidt-reaction:

4 g of sodium azide are added portionwise to 8.3 g of 7-methoxy-1-tetralone in 36 ml of acetic acid. Then 17 ml of concentrated sulphuric acid are added dropwise, without a rise in temperature over 40°; the solution is poured onto ice and neutralised with 2 N sodium hydroxide solution. The separating bulk of crystals is removed and recrystallised from ethyl acetate. One obtains 6.4 g of 8-methoxy-2,3,4,5-tetrahydro-1H-1-benzazepin-2-one (m.p. 137°–138°).

Methylation

The benzazepinone obtained by the Schmidt-reaction is N-methylated with sodium hydride and dimethyl sulphate analogously to Example 3 (b). After working up there are obtained 6.8 g of 8-methoxy-1-methyl-2,3,4,5-tetrahydro-1-H-1-benzazepin-2-one.

Hydrolysis

The methylbenzazepinone obtained by N-methylation is hydrolysed according to Example 1 (b) with excess potassium hydroxide in ethylenglycol monoethylether, worked up and used in (a) as aqueous-basic solution (pH 8.5).

EXAMPLE 19

Analogously to Example 18, one obtains, starting from 7-methoxy-1-tetralone, 6-methoxy-1-tetralone and 5-methoxy-1-tetralone by Schmidt-reaction (to the corresponding methoxy-2,3,4,5-tetrahydro-1-H-1-benzazepin-2-ones) with subsequent methylation and hydrolysis 4-(4-methoxy-2-N-methylaminophenyl)-butyric acid, 4-(5-methoxy-2-N-methylamino-phenyl)-butyric acid and 4-(6-methoxy-2-N-methylamino-phenyl)-butyric acid, the aqueous-basic solutions of which are acylated with appropriate benzoyl chlorides to the following compounds according to the invention:

(a) 4-[2-(N-methyl-4-chlorobenzamido)-4-methoxyphenyl]-butyric acid
$R^1$=—$OCH_3$, $R^3$=—$CH_3$, $R^4$=—Cl, $R^2$=$R^5$=$R^6$=—H, n=3
m.p. 107°–108° (from diethyl ether/petroleum ether)

(b) 4-[2-(N-methyl-3,4-dichlorobenzamido)-5-methoxyphenyl]-butyric acid
$R^1$=—$OCH_3$, $R^3$=—$CH_3$, $R^4$=$R^5$=—Cl, $R^2$=$R^6$=—H, n=3, m.p. 87°–88°

(c) 4-[2-(N-methyl-2,4-dichlorobenzamido)-5-methoxyphenyl]-butyric acid
$R^1$=—$OCH_3$, $R^3$=—$CH_3$, $R^4$=$R^5$=—Cl, $R^2$=$R^6$=—H, n=3, oil; sodium salt: m.p. 160° (decomposition)

(d) 4-[2-(N-methyl-4-chlorobenzamido)-6-methoxyphenyl)]-butyric acid
$R^1$=—$OCH_3$, $R^3$=—$CH_3$, $R^4$=—Cl, $R^2$=$R^5$=$R^6$=—H, n=3, m.p. 121°–122°

EXAMPLE 20

5-[2-(N-methyl-3-trifluoromethylbenzamido)-phenyl]-valeric acid $R^3$=—$CH_3$, $R^4$=—$CF_3$, $R^1$=$R^2$=$R^5$=$R^6$=—H, n=4

(a) The solution obtained according to (b) is reacted with 6.9 g of 3-trifluoromethylbenzoyl chloride analogously to Example 1 (a), whereby the observance of a weakly basic environment is ensured by an excess of sodium bicarbonate (23 g). Working up yields 8.8 g (68% of theory) of the title compound, m.p. 81°–83° C.

(b) Analogously to Example 18 (b), starting from 7.5 g of benzo-[b]-suberone, a ring expansion according to Schmidt to the corresponding lactam and following N-methylation is effected. The resulting 2-aza-2-methylbenzo-[c]-cyclooctanone (6.2 g as oil, 73% of theory) is hydrolysed in ethylenglycolmonoethylether with sodium hydroxide to 5-(2-N-methylaminophenyl)-valeric acid; the aqueous-basic solution is used under (a).

EXAMPLE 21

5-[2-(N-methyl-3,4-dichlorobenzamido)-phenyl]-valeric acid $R^3$=—$CH_3$, $R^4$=$R^5$=—Cl, $R^1$=$R^2$=$R^6$=—H, n=4

A solution of 5-(2-methylaminophenyl)-valeric acid prepared according to Example 20 (b) is reacted with 6.9 g of 3,4-dichlorobenzoyl chloride analogously to Example 1 (a). Working up and recrystallisation yield 3.7 g of the title compound, m.p. 86°–87°.

EXAMPLE 22

5-[2-(N-methyl-4-chlorobenzamido)-phenyl]-valeric acid $R^3$=—$CH_3$, $R^4$=—Cl, $R^1$=$R^2$=$R^5$=$R^6$=—H, n=4

(a) 2.5 g of potassium hydroxide in 25 ml of methanol are added to a solution of 5.4 g of diethyl-3-[2-(N-methyl-4-chloro-benzamido)phenyl]-propyl malonate in 50 ml of toluene. 4 days stirring at room temperature and extraction with chloroform yield the free 3-[2-(N-methyl-4-chlorobenzamido)-phenyl]-propyl-malonic acid, which splits off carbon dioxide while heating to 170°. Chromatographic purification of the residue and recrystallisation from ethyl acetate/petroleum ether (1:1) yield 1.5 g (36% of theory) of the title compound, m.p. 117°–118° C.

(b) 15.8 g of 3-[2-(N-methyl-4-chlorobenzamido)-phenyl]-propionic acid and 15 g of oxalyl chloride are stirred in toluene for 2 hours. After following evaporation in vacuo, the residue is taken up in 60 ml of dioxane and added dropwise to 1.6 g of sodium borohydride in 40 ml of dioxane. Heating to 100° is effected for 4 hours, followed by addition of 2 N hydrochloric acid in an ice bath to the end of the gas development. Extraction with diethyl ether yields 11.9 g of 3-[2-(N-methyl-4-chlorobenzamido)-phenyl]-propanol as oil, which is reacted without further purification in 80 ml of toluene with 3 g of pyridine and 6 g of tosyl chloride to the 3-[2-(N-methyl-4-chlorobenzamido)-phenyl]-propyl-tosylate (33 hours of stirring at room temperature). The chromatographic purification (silica gel, eluent methylene chloride) yields 6.1 g (31% of theory). This tosylate in 70 ml of ethanol is added dropwise to a solution of 0.35 g of sodium and 3.2 g of diethyl malonate in 60 ml of ethanol. Following heating under reflux for 24 hours, working up by extraction with methylene chloride and chromatographic purification with silica gel/-chloroform yield 5.4 g (89% of theory) of diethyl-3-[2-N-methyl-4-chlorobenzamido)-phenyl]-propyl malonate as oil, which is used under (a).

EXAMPLE 23

6-[2-(N-methyl-3-trifluoromethylbenzamido)-phenyl]-caproic acid $R^3 = -CH_3, R^4 = -CF_3, R^1 = R^2 = R^5 = R^6 = -H, n = 5$ 4.1 g of diethyl-4-[2-(N-methyl-3-trifluorobenzamido)-phenyl]-n-butyl malonate [prepared analogously to Example 22 (b) from 4-[2-(N-methyl-3-trifluoromethylbenzamido)-phenyl]butyric acid, via the corresponding butanol and butyltosylate, and the reaction with diethyl malonate] are saponificated with potassium hydroxide in toluene/methanol analogously to Example 22 (a) and without purification decarboxylated by heating. Recrystallisation from ethyl acetate/diethyl ether yields 1.9 g of the title compound, m.p. 103°–104° C.

EXAMPLE 24

Ampoules with 600 mg of 3-[2-N-methyl-4-chlorobenzamido)-phenyl]-propionic acid, batch size 250 kg, are produced as follows:

25 kg of 1,2-propyleneglycol and 150 kg of double-distilled water are provided, 15 kg of 3-[2-N-methyl-4-chlorobenzamido)-phenyl]propionic acid are added and, subsequently, 19 kg of sodium hydroxide solution (10% by weight NaOH) are slowly added, with stirring. When all has dissolved, the pH is adjusted to 7.5–8.0 with dilute hydrochloric acid. 0.0625 kg of sodium pyrosulphite are added and the mixture is stirred until all has dissolved. The volume is made up to 250 kg with double-distilled water. The solution is filled into 10 ml ampoules and sterilised at 120° for 30 minutes in an autoclave.

EXAMPLE 25

Ampoules with 600 mg of 4-[2-(N-methyl-4-chlorobenzamido)-phenyl]-butyric acid, batch size 250 kg, are produced as follows:

50 kg of 1,2-propyleneglycol and 150 kg of double-distilled water are provided. 15 kg of 4-[2-(N-methyl-4-chlorobenzamido)-phenyl]butyric acid is then added, with stirring. Subsequently, 18.5 kg of sodium hydroxide solution (10% by weight NaOH) is added and the solution is then adjusted to a pH of 8.0 with dilute hydrochloric acid. The volume is made up to 250 kg with double-distilled water. The solution is filled into 10 ml ampoules and sterilised at 120° for 30 minutes in an autoclave.

EXAMPLE 26

Tablets of 50 mg of
3-[2-(N-methyl-benzamido)-phenyl]-propionic acid are produced as follows:

25 kg of 3-[2-(N-methyl-benzamido)-phenyl]-propionic acid, 25 kg of xylitol and 26 kg of calcium phosphate are granulated with 2.5 kg of polyvinylpyrrolidone (molecular weight ~25000) in approximately 6 liters of water. The granulate is sieved through a sieve of 1.25 mm mesh size and, after drying, 8 kg of carboxymethylcellulose, 2.5 kg of talc and 1 kg of magnesium stearate are added. The dry granulate is compressed into tablets of 8 mm diameter, 250 mg weight and a hardness of 5–6 kg.

EXAMPLE 27

Tablets with 100 mg of 4-[2-(N-methyl-3,4-dichlorobenzamido)-phenyl]butyric acid are produced as follows:

40 kg of 4-[2-(N-methyl-3,4-dichlorobenzamido)-phenyl]-butyric acid, 24 kg of xylitol and 16 kg of calcium phosphate are granulated with 4 kg of polyvinylpyrrolidone (molecular weight ~25,000) in approximately 5.5 liters of water and pressed through a sieve of 1.25 mm mesh size. After drying, 10 kg of carboxymethylcellulose, 4 kg of talc and 2 kg of magnesium stearate are added. On an eccentric machine the granulate is compressed into tablets of 9 mm diameter, 250 mg weight and a hardness of 4–5 kg.

EXAMPLE 28

Tablets with 300 mg of 3-[2-(N-methyl-3,4-dichlorobenzamido)-5-chlorophenyl]-propionic acid are produced as follows:

60 kg of 3-[2-(N-methyl-3,4-dichloro-benzamido)-5-chloro-phenyl]propionic acid, 12 kg of xylit and 8 kg of calcium phosphate are granulated with 4 kg of polyvinylpyrrolidone (molecular weight ~25,000) in approximately 6 liters of water and pressed through a sieve of 1.25 mm mesh size. After drying, 10 kg of carboxymethylcellulose, 4 kg of talc and 2 kg of magnesium stearate are added. On a revolver machine the granulate is compressed into tablets of 11 mm diameter, 500 mg weight and a hardness of 6–7 kg.

EXAMPLE 29

10,000 capsules with an active substance content of 50 mg of 4-[2-(N-methyl-4-chlorobenzamido)-phenyl]-butyric acid are prepared from the following constituents:

500 g of 4-[2-(N-methyl-4-chlorobenzamido)-phenyl]-butyric acid, 495 g of microcrystalline cellulose and 5 g of amorphous silicic acid are thoroughly mixed and filled into hard gelatin capsules size 4.

EXAMPLE 30

10,000 capsules with an active substance content of 50 mg of 4-[2-(N-methyl-3-trifluoromethylbenzamido)-phenyl]-butyric acid are prepared from the following constituents:

500 g of 4-[2-(N-methyl-3-trifluoromethylbenzamido)-phenyl]-butyric acid, 495 g of microcrystalline cellulose and 5 g of amorphous silicic acid are thoroughly mixed and filled into hard gelatin capsules size 4.

Pharmacology

The ω-[2-(N-lower alkyl-benzamido)-phenyl]-alkanoic acids and their salts lower the blood glucose level, whereby they differ in their chemical structure and their mode of action fundamentally from pancreas effective, betacytotropic substances (e.g. sulphonyl urea) by their extrapancreatic, particularly hepatic action; they prove superior to extrapancreatic active preparations, e.g. buformin and phenformin.

In the following Table, the compounds investigated are characterised by a serial number, which is to be assigned as follows:

| Serial No. | Name of compound |
|---|---|
| 1 | buformin |

| Serial No. | Name of compound |
|---|---|
| 2 | phenformin |
| 3 | 4-[2'-(N-methyl-benzamido)-phenyl]-butyric acid |
| 4 | 3-[2(N-methyl-4-chlorobenzamido)-phenyl]-propionic acid |
| 5 | 3-[2-(N-methyl-3,4-dichloro-benzamido)-phenyl]-propionic acid |
| 6 | 3-[2-(N-methyl-benzamido)-phenyl]-propionic acid |
| 7 | 3-[5-chloro-2-(N-methyl-3,4-dichloro-benzamido)-phenyl]-propionic acid |
| 8 | 3-[5-chloro-2-(N-methyl-3-trifluoromethylbenazmido)-phenyl]-propionic acid |
| 9 | 4-[2-(N-methyl-4-chlorobenzamido)-phenyl]-butyric acid |
| 10 | 4-[2-(N-methyl-3,4-dichloro-benzamido)-phenyl]-butyric acid |
| 11 | 4-[2-(N-methyl-2,4-dichloro-benzamido)-phenyl]-butyric acid |
| 12 | 4-[2-(N-methyl-3-trifluoromethylbenzamido)-phenyl]-butyric acid |
| 13 | 4-[6-methoxy-2-(N-methyl-4-chlorobenzamido)-phenyl]-butyric acid |
| 14 | 4-[5-methoxy-2-(N-methyl-3,4-dichloro-benzamido)-phenyl]-butyric acid |
| 15 | 5-[2-(N-methyl-3,4-dichloro-benzamido)-phenyl]-valeric acid |

In Table I there are reproduced investigations of the influence of representatives of the compounds according to the invention on the blood glucose concentration of fasting, metabolically healthy rats after single oral administration of substance of 0.6 to 1.0 mmole/kg body weight within 24 hours. Column A states in each case the maximal lowering in % with reference to the control group within 24 hours after application of the compounds.

Column 8 shows simultaneously the dose of active principle (mg/kg), which effects in 50% of the animals a lowering of the blood glucose concentration by at least 15% with reference to the control group.

In column C data on the acute toxicity ($LD_{50}$ mouse, per os) are reproduced.

The values in column D show the concentrations ($ID_{50}$ mmol/l) of the substances in the perfusate, which bring about on the isolatedly perfused rat liver an inhibition of the glucose formation from lactat and pyruvat by 50%.

TABLE I

| Compound Serial No. | A Change of the blood glucose concentration in % | B $ED_{50}$ (mg/kg) | C $LD_{50}$ (mg/kg) | D $ID_{50}$ (mmol/kg) |
|---|---|---|---|---|
| 1 | −20 | 227 | 475 | ineffective |
| 2 | −2 | not determinable | 410* | ineffective |
| 3 | −27 | 205 | — | — |
| 4 | −16 | 426 | — | 0.140 |
| 5 | −11 | 363 | 1100 | 0.100 |
| 6 | −26 | 221 | 970 | 0.200 |
| 7 | −15 | — | >1000 | 0.034 |
| 8 | −26 | 185 | >1000 | 0.105 |
| 9 | −24 | 103 | >1000 | 0.125 |
| 10 | −17 | 198 | 250 (i.p.) | 0.035 |
| 11 | −17 | 245 | >1000 | 0.060 |
| 12 | −20 | 278 | 150 (i.p.) | 0.015 |
| 13 | −14 | >500 | — | 0.044 |
| 14 | −21 | — | — | 0.070 |
| 15 | −5 | >700 | — | 0.050 |

*cited according to D. A. Blickens and S. J. Riggi, Toxicol. Appl. Parmacol. 14 (1969) 393–400

To Table I:
A = maximal change of the blood glucose concentration (in %) in vivo with reference to control animals
B = dose, which effects a lowering of the blood glucose concentration by 15% in 50% of the animals
C = toxicity
D = dose, which brings about an inhibition of the glucose formation from lactat and pyruvat by 50%.

The compounds according to the invention are distinguished vis-à-vis the comparative compounds through a lower toxicity and, in part, through a stronger and continuous hypoglycaemic action. In addition they are characterised by a substantially stronger inhibition of the glucose formation from lactate and pyruvate in the liver. Whereas buformin and phenformin cause no inhibition, with the compounds according to the invention inhibitory effects of up to 100% may be achieved.

The determination of the pharmacological properties was effected according to the following methods:

1. Blood Glucose Determination After Single Oral Application

Young male Sprague-Dawley rats (body weight 160–200 g) are used. The animals are kept in makralon cages with up to 5 animals per cage [room-temperature 23° C., humidity of the atmosphere 55%, fixed day-/night rhythm (12/12 h), rat standard diet Altromin$^R$].

Food is withdrawn from the animals 20-22 hours before the taking of the 1st blood sample. Water uptake occurs ad libitum. Blood samples are taken at intervals of 0, 2, 6 and 24 hours through puncture from the postorbital plexus.

After deproteinisation with perchloric acid, the blood glucose determination is effected by means of the enzymatic HK/G-6-POH method according to R. Richterich [Klinische Chemie, Theorie und Praxis, 3rd Edition, 1971, S. Karger Verlag, Zuerich-Basle, page 275].

For comparison, in each case a control group treated with pure solvent is also investigated.

2. Inhibition of Glucose Formation on the Isolatedly Perfused Rat Liver

Young male Sprague-Dawley rats (160–200 g) are used. The animals are kept as described under 1.

Food is withdrawn from the animals 20-22 hours before the operation. Water uptake occurs ad libitum. Operation and perfusion of the liver are effected according to the technique of R. Scholz et al. [Eur. J. Biochem. 38 (1973) 64–72]. As perfusion liquids, Krebs-Henseleit biocarbonate buffer (pH 7.4) is used which is saturated with an oxygen/carbon dioxide mixture (95/5) and contains 1.6 mmoles/liter L-lactates and 0.2 mmole/liter pyruvate. The perfusion liquid is pumped into the liver via a cannula introduced into the portal vein. The perfusion liquid emerging is collected via a cannula introduced into the vena cava and then taken past an oxygen electrode. The liver is perfused for about 2 hours. The test compounds are infused from the 32nd to 80th minute of the perfusion, with increasing concentrations (0.01, 0.03, 0.10 mmol/l).

Samples of the emerged perfusion liquid are collected at one-minute intervals and analysed for glucose, lactate and pyruvate according to enzymatic standard methods. The oxygen content is continuously determined by means of a platinum electrode. The check constants ($ID_{50}$) stated in Table I refer to the state which exists before and after addition of the compounds; the changes caused alone through lactate and pyruvate were set at 100%.

3. Determination of the toxicity

The toxicity investigations were carried out on female NMRI mice (body weight 22–26 g). The animals (5 animals per dose) receive, 18 hours before the treatment, the food (Altromin ®) reduced to 50 g/50 animals and water ad libitum. Various doses of the substances are administered per os or intraperitoneal (volume 20 ml/kg). The duration of observation is 7 days. The $DL_{50}$, i.e. the dose at which 50% of the animals die, is determined graphically from the dose effect curve.

We claim:

1. A method of treating a patient afflicted with or subject to a glucose-metabolism disturbance which comprises administering to the patient an effective amount of a medicament preparation having a physiologically-active ingredient and pharmacologically-compatible excipient, the physiologically-active ingredient being an ω-[2-{-N-lower alkyl)benzamide}phenyl]-alkanoic acid of the formula

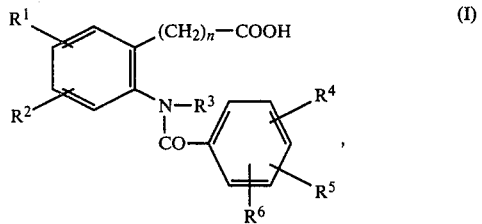

wherein
n denotes a positive whole number from 2 to 5,
$R^1$ denotes a hydrogen atom, halo, lower alkyl, lower alkoxy, lower alkylmercapto, trifluoromethyl or optionally-(halo- or lower-alkoxy-)substituted phenyl,
$R^2$ denotes a hydrogen atom, halo, lower alkyl or lower alkoxy,
$R^3$ denotes lower alkyl,
$R^4$ denotes a hydrogen atom, halo, hydroxyl, lower alkyl, lower alkoxy, lower alkylmercapto, optionally-(halo- or nitro-)substituted phenyl, nitro, optionally-(lower alkylated) amino, lower alkylcarbonyl, optionally-halosubstituted benzoyl, trifluoromethyl, trifluoromethoxy or trifluoromethylmercapto,
$R^5$ denotes a hydrogen atom, halo, lower alkyl or lower alkoxy,
$R^6$ denotes a hydrogen atom, lower alkyl or lower alkoxy, or a pharmacologically-acceptable salt thereof.

2. A method according to claim 1 for treating a patient afflicted with or subject to a glucose-metabolism disturbance which comprises administering to the patient an effective amount of a medicament preparation having a physiologically-active ingredient and pharmacologically-compatible excipient, the physiologically-active ingredient being an ω-[2-{N-(lower alkyl)benzamido}phenyl]alkanoic acid of the formula

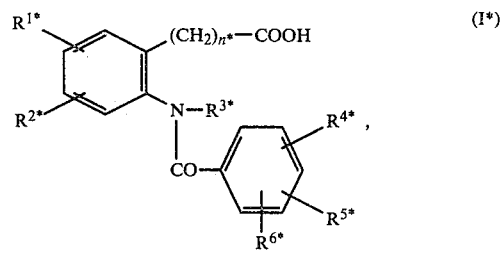

wherein
n* denotes a positive whole number from 2 to 5,
$R^{1*}$ denotes a hydrogen atom, chloro, bromo, lower alkyl, methoxy or phenyl,
$R^{2*}$ denotes a hydrogen atom, chloro, bromo, methyl or methoxy,
$R^{3*}$ denotes straight-chain lower alkyl,
$R^{4*}$ denotes a hydrogen atom, fluoro, chloro, bromo, lower alkyl, hydroxyl, lower alkoxy, phenyl, nitro, amino, dimethylamino or trifluoromethyl,
$R^{5*}$ denotes a hydrogen atom, chloro, lower alkyl or lower alkoxy,
$R^{6*}$ denotes a hydrogen atom, lower alkyl or lower alkoxy,
or a pharmacologically-acceptable salt thereof.

3. A method according to claim 1 for treating a patient afflicted with or subject to a glucose-metabolism disturbance which comprises administering to the patient an effective amount of a medicament preparation having a physiologically-active ingredient and pharmacologically-compatible excipient, the physiologically-active ingredient being an ω-[2-{N-(lower alkyl)benzamido}phenyl]alkanoic acid of the formula

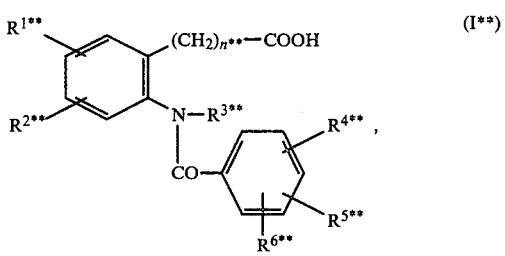

wherein
n** denotes a positive whole number from 2 to 5,
$R^{1**}$ denotes a hydrogen atom, methyl, methoxy, chloro, bromo or phenyl,
$R^{2**}$ denotes a hydrogen atom, chloro or methyl,
$R^{3**}$ denotes straight-chain alkyl with from 1 to 4 carbon atoms,
$R^{4**}$ denotes a hydrogen atom, chloro, bromo, methyl, lower alkoxy, phenyl or trifluoromethyl,
$R^{5**}$ denotes a hydrogen atom, chloro, lower alkyl or methoxy,
$R^{6**}$ denotes a hydrogen atom, lower alkyl or methoxy,
or a pharmacologically-acceptable salt thereof.

4. A method according to claim 1 for treating a patient afflicted with or subject to a glucose-metabolism disturbance which comprises administering to the patient an effective amount of a medicament preparation having a physiologically-active ingredient and pharmacologically-compatible excipient, the physiologically-active ingredient being an ω-[2-{N-(lower alkyl)benzamido}phenyl]alkanoic acid of the formula

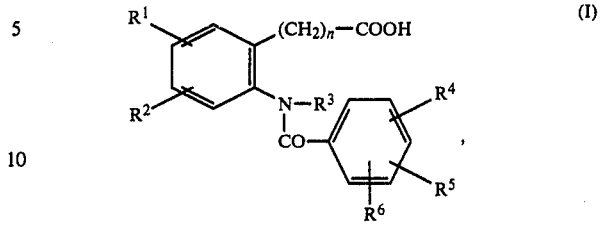

the physiologically-active ingredient being an alkanoic acid of the formula (I)

wherein
n denotes a positive whole number from 3 to 5,
$R^1$ denotes a hydrogen atom, halo, lower alkyl, lower alkoxy, lower alkylmercapto, trifluoromethyl or optionally-(halo- or lower-alkoxy-)substituted phenyl,
$R^2$ denotes a hydrogen atom, halo, lower alkyl or lower alkoxy,
$R^3$ denotes lower alkyl,
$R^4$ denotes a hydrogen atom, halo, hydroxyl, lower alkyl, lower alkoxy, lower alkylmercapto, optionally-(halo- or nitro-)substituted phenyl, nitro, optionally-(lower alkylated) amino, lower alkylcarbonyl, optionally-halosubstituted benzoyl, trifluoromethyl, trifluoromethoxy or trifluoromethylmercapto,
$R^5$ denotes a hydrogen atom, halo, lower alkyl or lower alkoxy,
$R^6$ denotes a hydrogen atom, lower alkyl or lower alkoxy,
or a pharmacologically-acceptable salt thereof,
the preparation comprising from 10 to 1000 milligrams of said physiologically-active ingredient per unit dose.

10. An ω-[2-{N-(lower alkyl)benzamido}phenyl]butyric acid of the formula

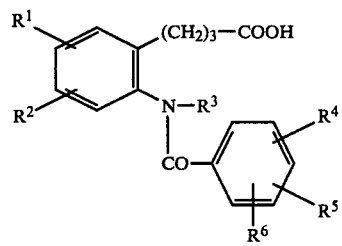

wherein
$R^1$ denotes a hydrogen atom, halo, lower alkyl, lower alkoxy, lower alkylmercapto, trifluoromethyl or optionally-(halo- or lower-alkoxy-)substituted phenyl,
$R^2$ denotes a hydrogen atom, halo, lower alkyl or lower alkoxy,
$R^3$ denotes lower alkyl,
$R^4$ denotes a hydrogen atom, halo, hydroxyl, lower alkyl, lower alkoxy, lower alkylmercapto, optionally-(halo- or nitro-)substituted phenyl, nitro, optionally-(lower alkylated) amino, lower alkylcarbonyl, optionally-halosubstituted benzoyl, trifluoromethyl, trifluoromethoxy or trifluoromethylmercapto,
$R^5$ denotes a hydrogen atom, halo, lower alkyl or lower alkoxy,
$R^6$ denotes a hydrogen atom, lower alkyl or lower alkoxy,
or a pharmacologically-acceptable salt thereof.

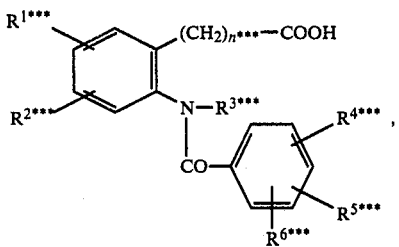

(I***)

wherein
n*** denotes 2 or 3,
$R^{1***}$ denotes a hydrogen atom, chloro, methyl or methoxy,
$R^{2***}$ denotes a hydrogen atom or methyl,
$R^{3***}$ denotes methyl or ethyl,
$R^{4***}$ denotes a hydrogen atom, chloro, phenyl or trifluoromethyl,
$R^{5***}$ denotes a hydrogen atom or chloro,
$R^{6***}$ denotes a hydrogen atom,
or a pharmacologically-acceptable salt thereof.

5. A method according to claim 1 for treating a patient afflicted with or subject to a glucose-metabolism disturbance which comprises administering to the patient an effective amount of a medicament preparation having a physiologically-active ingredient and pharmacologically-compatible excipient, the physiologically-active ingredient being an ω-[2-{N-(lower alkyl)benzamido}phenyl]alkanoic acid of the formula

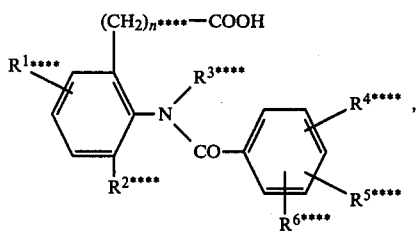

(I****)

wherein
n**** denotes 2 or 3,
$R^{1****}$ denotes a hydrogen atom, chloro, methyl or methoxy,
$R^{2****}$ denotes a hydrogen atom,
$R^{3****}$ denotes methyl,
$R^{4****}$ denotes a hydrogen atom, chloro or trifluoromethyl,
$R^{5****}$ denotes a hydrogen atom or chloro,
$R^{6****}$ denotes a hydrogen atom,
or a pharmacologically-acceptable salt thereof.

6. A method according to claim 1 for treating a patient afflicted with or subject to a glucose-metabolism disturbance which comprises administering to the patient an effective amount of a medicament preparation having a physiologically-active ingredient and pharmacologically-compatible excipient, the physiologically-active ingredient being 3-[2-(N-methylbenzamido)-phenyl]propionic acid.

7. A method according to claim 1 wherein the medicament preparation comprises from 10 to 1000 milligrams of said physiologically-active ingredient.

8. A method according to claim 1 wherein n is 2.

9. A medicament preparation having a physiologically-active ingredient and pharmaceutically-compatible excipient, 11. An ω-[2-{N-(lower alkyl)benzamido}phenyl]valeric acid of the formula

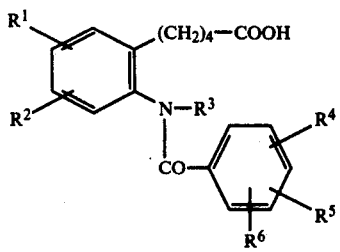

wherein
R¹ denotes a hydrogen atom, halo, lower alkyl, lower alkoxy, lower alkylmercapto, trifluoromethyl or optionally-(halo- or lower-alkoxy-)substituted phenyl,
R² denotes a hydrogen atom, halo, lower alkyl or lower alkoxy,
R³ denotes lower alkyl,
R⁴ denotes a hydrogen atom, halo, hydroxyl, lower alkyl, lower alkoxy, lower alkylmercapto, optionally-(halo- or nitro-)substituted phenyl, nitro, optionally-(lower alkylated) amino, lower alkylcarbonyl, optionally-halosubstituted benzoyl, trifluoromethyl, trifluoromethoxy or trifluoromethylmercapto,
R⁵ denotes a hydrogen atom, halo, lower alkyl or lower alkoxy,
R⁶ denotes a hydrogen atom, lower alkyl or lower alkoxy,
or a pharmaceutically-acceptable salt thereof.

12. An ω-[2-{N-(lower alkyl)benzamido}phenyl]caproic acid of the formula

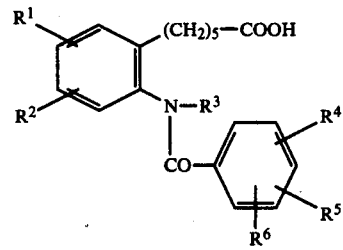

wherein
R¹ denotes a hydrogen atom, halo, lower alkyl, lower alkoxy, lower alkylmercapto, trifluoromethyl or optionally-(halo- or lower alkoxy-)substituted phenyl,
R² denotes a hydrogen atom, halo, lower alkyl or lower alkoxy,
R³ denotes lower alkyl,
R⁴ denotes a hydrogen atom, halo, hydroxyl, lower alkyl, lower alkoxy, lower alkylmercapto, optionally-(halo- or nitro-)substituted phenyl, nitro, optionally-(lower alkylated) amino, lower alkylcarbonyl, optionally-halosubstituted benzoyl, trifluoromethyl, trifluoromethoxy or trifluoromethylmercapto,
R⁵ denotes a hydrogen atom, halo, lower alkyl or lower alkoxy,
R⁶ denotes a hydrogen atom, lower alkyl or lower alkoxy,
or a pharmaceutically-acceptable salt thereof.

13. 4-[2-(N-methyl-3,4-dichlorobenzamido)phenyl]butyric acid.

14. A method according to claim 1 wherein the glucose-metabolism disturbance is diabetes.

* * * * *